United States Patent
Engqvist et al.

(10) Patent No.: US 9,676,665 B2
(45) Date of Patent: Jun. 13, 2017

(54) STORAGE STABLE PREMIXED HYDRAULIC CEMENT COMPOSITIONS, CEMENTS, METHODS, AND ARTICLES

(75) Inventors: Håkan Engqvist, Östhammar (SE); Jonas Aberg, Uppsala (SE)

(73) Assignee: OSSDSIGN AB, Uppsala (SE)

( * ) Notice: Subject to any disclaimer, the term of this patent is extended or adjusted under 35 U.S.C. 154(b) by 587 days.

(21) Appl. No.: 14/343,105

(22) PCT Filed: Sep. 10, 2012

(86) PCT No.: PCT/IB2012/054701
§ 371 (c)(1),
(2), (4) Date: Jul. 10, 2014

(87) PCT Pub. No.: WO2013/035083
PCT Pub. Date: Mar. 14, 2013

(65) Prior Publication Data
US 2014/0312517 A1    Oct. 23, 2014

Related U.S. Application Data

(63) Continuation-in-part of application No. 13/229,534, filed on Sep. 9, 2011, now abandoned, which is a continuation-in-part of application No. 13/229,539, filed on Sep. 9, 2011, now abandoned, which is a continuation-in-part of application No. 13/229,545, filed on Sep. 9, 2011, now Pat. No. 8,591,645.

(60) Provisional application No. 61/533,064, filed on Sep. 9, 2011.

(51) Int. Cl.
| | | |
|---|---|---|
| C04B 12/02 | (2006.01) |
| C04B 28/34 | (2006.01) |
| A61B 17/88 | (2006.01) |
| C04B 111/00 | (2006.01) |
| A61B 17/56 | (2006.01) |

(52) U.S. Cl.
CPC ........ C04B 12/025 (2013.01); A61B 17/8802 (2013.01); C04B 28/344 (2013.01); A61B 17/56 (2013.01); C04B 2111/00836 (2013.01); Y10T 428/131 (2015.01)

(58) Field of Classification Search
CPC .............. C04B 12/025; C04B 28/344; C04B 2111/00836; A61B 17/56; A61B 17/8802
See application file for complete search history.

(56) References Cited

U.S. PATENT DOCUMENTS

| | | |
|---|---|---|
| 5,152,836 A | 10/1992 | Hirano et al. |
| 5,338,356 A | 8/1994 | Hirano et al. |
| 5,503,164 A | 4/1996 | Friedman |
| 5,605,713 A | 2/1997 | Boltong |
| 5,683,667 A | 11/1997 | Fulmer et al. |
| 5,782,971 A | 7/1998 | Constantz et al. |
| 5,783,217 A | 7/1998 | Lee et al. |
| 6,027,742 A * | 2/2000 | Lee ............ A61F 2/28 423/308 |
| 6,117,456 A | 9/2000 | Lee et al. |
| 6,206,957 B1 | 3/2001 | Wenz et al. |
| 6,214,368 B1 * | 4/2001 | Lee ............ A61F 2/28 424/423 |
| 6,331,312 B1 * | 12/2001 | Lee ............ A61F 2/28 424/422 |
| 6,338,810 B1 | 1/2002 | Carpena |
| 6,425,949 B1 * | 7/2002 | Lemaitre ............ A61L 24/0084 106/35 |
| 6,521,246 B2 | 2/2003 | Sapieszko et al. |
| 6,642,285 B1 | 11/2003 | Bohner et al. |
| 6,733,582 B1 | 5/2004 | Bohner et al. |
| 6,863,899 B2 | 3/2005 | Koblish et al. |
| 6,905,516 B1 | 6/2005 | Lemaitre et al. |
| 6,991,803 B2 | 1/2006 | Sapieszko et al. |
| 7,118,705 B2 | 10/2006 | Lin |
| 7,175,858 B2 | 2/2007 | Constantz et al. |
| 7,252,841 B2 | 8/2007 | Constantz et al. |

(Continued)

FOREIGN PATENT DOCUMENTS

| | | |
|---|---|---|
| CN | 1919357 A | 2/2007 |
| EP | 543765 A1 | 5/1993 |

(Continued)

OTHER PUBLICATIONS

Bohner et al, J. Biomaterials, 26(33):6423-6429 (2005).
Xu et al, Journal of Materials Science: Materials in Medicine, 18(7):1345-1353 (2007).
Barralet et al, J. Biomaterials, 25(11):2197-2203 (2004).
Habraken et al, Advance Drug Delivery Reviews, 59(4-5):234-248 (2007).
Han et al, Acta Biomaterialia, 5:3165-3177 (2009).
Desai et al, Advances in Bioceramics and Biocomposites II, Ceramic Engineering and Science Proceedings, vol. 27, Issue 6, Wereszczak et al, Editor, Wiley, pp. 61-69 (Nov. 2006).
Hirayama et al, Journal of Research of the National Institute of Standards and Technology, 113(6):311-320 (2008).

*Primary Examiner* — Anthony J Green
(74) *Attorney, Agent, or Firm* — Porter Wright Morris & Arthur LLP

(57) ABSTRACT

Refrigerated hydraulic cement compositions comprise a mixture of (a) β-tricalcium phosphate powder, (b) monocalcium phosphate comprising monocalcium phosphate anhydrous (MCPA), monocalcium phosphate monohydrate (MCPM), or a combination thereof, wherein a 0.1 g/ml saturated aqueous solution of the monocalcium phosphate has a pH less than 3.0, (c) non-aqueous water-miscible liquid, and (d) an aqueous hydrating liquid. The aqueous hydrating liquid is included in an amount of about 1-50 volume percent, based on the combined volume of the non-aqueous water-miscible liquid and the aqueous hydration liquid, and the refrigerated hydraulic cement composition is storage stable for greater than one day, without setting. Methods of forming hardened cements in vivo and/or for forming implants for use in vivo employ the hydraulic cement compositions.

29 Claims, 3 Drawing Sheets

(56) References Cited

U.S. PATENT DOCUMENTS

| | | |
|---|---|---|
| 7,318,841 B2 | 1/2008 | Tofighi et al. |
| 7,351,280 B2 | 4/2008 | Khairoun et al. |
| 7,407,542 B2 | 8/2008 | Lemaitre et al. |
| 7,473,312 B2 | 1/2009 | Barralet et al. |
| 7,501,018 B2 | 3/2009 | Engqvist et al. |
| 7,709,029 B2 | 5/2010 | Chow et al. |
| 7,754,246 B2 | 7/2010 | Mosley et al. |
| 8,282,396 B2 | 10/2012 | Chow et al. |
| 8,591,645 B2 | 11/2013 | Engqvist et al. |
| 2003/0082232 A1 | 5/2003 | Lee et al. |
| 2003/0199615 A1 | 10/2003 | Chaput et al. |
| 2004/0086573 A1* | 5/2004 | Liu ................... A61L 24/02 424/601 |
| 2006/0239884 A1 | 10/2006 | Chane-Ching et al. |
| 2006/0263443 A1 | 11/2006 | Chow et al. |
| 2007/0092856 A1 | 4/2007 | Chow et al. |
| 2007/0189951 A1 | 8/2007 | Constantz et al. |
| 2008/0027455 A1 | 1/2008 | Bondeville |
| 2008/0028992 A1 | 2/2008 | Lee et al. |
| 2008/0187571 A1 | 8/2008 | Clineff et al. |
| 2008/0206300 A1 | 8/2008 | Bohner et al. |
| 2009/0022771 A1 | 1/2009 | Lynn et al. |
| 2009/0220475 A1 | 9/2009 | Bohner et al. |
| 2010/0095870 A1 | 4/2010 | Insley et al. |
| 2010/0269736 A1 | 10/2010 | Chow et al. |
| 2010/0303888 A1 | 12/2010 | Barralet et al. |
| 2011/0014244 A1 | 1/2011 | Sapieszko et al. |
| 2011/0152195 A1 | 6/2011 | O'Mahony et al. |
| 2011/0158963 A1 | 6/2011 | Font Perez et al. |
| 2012/0022023 A1 | 1/2012 | Engqvist et al. |
| 2012/0058152 A1 | 3/2012 | Garcia De Castro Andrews et al. |
| 2012/0330435 A1 | 12/2012 | Engqvist et al. |
| 2013/0138114 A1 | 5/2013 | Lin et al. |

FOREIGN PATENT DOCUMENTS

| | | |
|---|---|---|
| EP | 1023032 B1 | 1/2002 |
| EP | 936929 B1 | 6/2004 |
| EP | 1380313 B1 | 5/2005 |
| EP | 1298103 B1 | 5/2011 |
| JP | 1-100049 A | 4/1989 |
| WO | 02/11781 A1 | 2/2002 |
| WO | 2004/093734 A2 | 11/2004 |
| WO | 2005/074453 A2 | 8/2005 |
| WO | 2005/077049 A2 | 8/2005 |
| WO | 2007/047921 A2 | 4/2007 |
| WO | 2009/077210 A1 | 6/2009 |
| WO | WO2009/108934 A2 * | 9/2009 |
| WO | 2010/055483 A2 | 5/2010 |
| WO | 2010/092001 A1 | 8/2010 |
| WO | 2011/009635 A1 | 1/2011 |

\* cited by examiner

STORAGE STABLE PREMIXED HYDRAULIC CEMENT COMPOSITIONS, CEMENTS, METHODS, AND ARTICLES

The present application is a 371 of PCT/IB2012/054701 filed Sep. 10, 2012, and claims priority under 35 U.S.C. 120 as a continuation-in-part of (i) U.S. application Ser. No. 13/229,534 filed Sep. 9, 2011, now abandoned, (ii) U.S. application Ser. No. 13/229,539 filed Sep. 9, 2011, now abandoned, and (iii) U.S. application Ser. No. 13/229,545 filed Sep. 9, 2011, now U.S. Pat. No. 8,591,645 B2, and claims priority under 35 U.S.C. 119 of U.S. Application Ser. No. 61/533,064 filed Sep. 9, 2011.

FIELD OF THE INVENTION

The present invention is directed to storage stable hydraulic cement compositions, and, more particularly, to premixed storage stable hydraulic cement compositions in a refrigerated form. The hydraulic cement compositions may be formed into hardened cements by removal from refrigerated conditions. In certain embodiments, the hydraulic cements are suitable for use as biomaterials for in vivo delivery, for example for bone and tooth-root restoration. The invention is also directed to hardened cements, methods of preparing hardened cements, and articles of manufacture including, inter alia, such hydraulic cement compositions.

BACKGROUND OF THE INVENTION

Self-hardening calcium phosphate cements (CPC) have been used for bone and tooth restoration and for local drug delivery applications. See, for example, Larsson et al, "Use of injectable calcium phosphate cement for fracture fixation: A review," *Clinical Orthopedics and Related Research*, 395:23-32 (2002) and Oda et al, "Clinical use of a newly developed calcium phosphate cement (XSB-671D)," *Journal of Orthopedic Science*, 11(2):167-174 (2006). The cements in powder form are typically mixed with an aqueous solution immediately before application. In the clinical situation, the ability of the surgeon to properly mix the cement powder and hydrating liquid and then place the cement paste in a defect within the prescribed time is a crucial factor in achieving optimum results. Specifically, the dry cement powder material needs to be mixed with an aqueous solution in the surgical setting, i.e., the operating room, transferred to an applicator, typically a syringe, and delivered to the desired location within the setting time. Conventional cements generally have a setting time of about 15-30 minutes. However, the methods used for mixing and transfer of cement for injection in the operating room are technically difficult and pose a risk for non-optimal material performance, e.g., early setting renders materials difficult to inject or causes phase separation, so-called filter pressing. Further, for technical reasons and time constraints, the material is typically mixed with a hydrating liquid in bulk to form a paste and the paste is then transferred to smaller syringes for delivery. In practice, material is often wasted due to an early setting reaction, i.e., the hydrated material sets to a hardened cement prior to delivery to the desired location, or because more material than is needed is mixed. A solution to these problems that includes the possibility to deliver material in smaller quantities in a more controlled manner is thus desired. Additionally, handling premixed formulations can be problematic if they are too viscous to deliver by injection.

The problem of obtaining a proper mix of the powder material and hydrating liquid for optimum clinical results in apatite cements has been addressed in US 2006/0263443, US 2007/0092856, Carey et al, "Premixed rapid-setting calcium phosphate composites for bone repair," *Biomaterials*, 26(24):5002-5014 (2005), Takagi et al, "Premixed calcium-phosphate cement pastes," *Journal of Biomedical Materials Research Part B-Applied Biomaterials*, 67B(2): 689-696 (2003), Xu et al, "Premixed macroporous calcium phosphate cement scaffold," *Journal of Materials Science-Materials in Medicine*, 18(7):1345-1353 (2007), and Xu et al, "Premixed calcium phosphate cements: Synthesis, physical properties, and cell cytotoxicity," *Dental Materials*, 23(4):433-441 (2007), wherein premixed pastes are described. In US 2006/0263443, for example, a powder composition for hydroxyapatite is premixed with an organic acid and glycerol to form a paste, which paste may subsequently be injected into a defect. The injected material hardens through the diffusion of body liquids into the biomaterial. The organic acid is added to increase resistance to washout and the end product after setting is apatite, which is known to have a long resorption time in vivo as described above. Also, compositions of β-tricalcium phosphate (β-TCP) and hydrated acid calcium phosphate in glycerin or polyethylene glycol have previously been described in CN 1919357, Han et al, "β-TCP/MCPM-based premixed calcium phosphate cements," *Acta Biomaterialia, doi:*10.1016/j.actbio.2009.04.024 (2009) and Aberg et al, "Premixed acidic calcium phosphate cement: characterization of strength and microstructure, *Journal of Biomedical Materials Research*, 2010, May; 93(2):436-41. However, it is difficult to obtain sufficient shelf life using the described formulations in the prior art, as also noted by Shimada et al, *Journal of Research of the National Institute of Standards and Technology* "Properties of Injectable Apatite-Forming Premixed Cements," 115(4): 240 (July-August 2010). Shelf life is also a problem for reactive Brushite forming cements. Tests have been performed using monocalcium phosphate anhydrous (MCPA), where difficulties to achieve a rapid setting time resulted when changing from MCPM (monocalcium phosphate monohydrate) to MCPA.

Thus, there is a continuing need to be able to efficiently prepare, store and safely deliver hydraulic cements, particularly for biomedical applications, i.e., hydraulic cements that overcome the above noted and/or other difficulties of conventional hydraulic cement materials, while optionally optimizing performance properties, particularly in vivo performance properties.

SUMMARY OF THE INVENTION

Accordingly, it is an object of the present invention to provide hydraulic cements, and hardened cements, methods, and articles of manufacture based on the hydraulic cements, with an optimized handling and biological response for clinical use.

In one embodiment, the invention is directed to a refrigerated hydraulic cement composition, comprising a mixture of (a) β-tricalcium phosphate powder, (b) monocalcium phosphate comprising monocalcium phosphate anhydrous (MCPA), monocalcium phosphate monohydrate (MCPM), or a combination thereof, wherein a 0.1 g/ml saturated aqueous solution of the monocalcium phosphate has a pH less than 3.0, (c) non-aqueous water-miscible liquid, and (d) an aqueous hydrating liquid, wherein the aqueous hydrating liquid is included in an amount of about 1-50 volume percent, based on the combined volume of the non-aqueous water-miscible liquid and the aqueous hydration liquid. The refrigerated hydraulic cement composition is storage stable for greater than one day, without setting to a hardened cement.

The invention is also directed to methods of producing a hardened cement with such compositions, hardened cements produced from such compositions, and articles of manufacture including such compositions.

In yet another embodiment, the invention is directed to a method of manufacturing an implant, comprising a) filling a mould with a mixture of (i) a nonhydrated cement powder composition, and (ii) a non-aqueous water-miscible liquid, (b) exposing the filled mould to a temperature greater than 25° C., and, optionally, an aqueous environment, to harden the mixture, (c) removing the mould to provide a shaped implant, and (d) exposing the shaped implant to an aqueous environment to remove non-aqueous water-miscible liquid from the shaped implant. In a specific embodiment, the cement powder composition comprises monocalcium phosphate comprising monocalcium phosphate anhydrous (MCPA), monocalcium phosphate monohydrate (MCPM), or a combination thereof, and forms monetite cement.

In another specific embodiment, the invention is directed to a hydraulic cement composition which comprises a mixture of (a) a non-hydrated powder composition comprising calcium silicate powder (b) non-aqueous water-miscible liquid, and (c) a hydration liquid.

In a further specific embodiment, the invention is directed to a hydraulic cement composition which comprises a mixture of (a) a non-hydrated powder composition comprising calcium aluminate powder, (b) non-aqueous water-miscible liquid, and (c) a hydration liquid.

The hydraulic cement compositions according to the invention are advantageous in that they avoid many of the preparation difficulties of conventional hydraulic cement compositions, particularly when used as biomaterials, and may be easily handled and efficiently delivered to a desired location, without excessive material waste, premature setting, or other problems often encountered in prior cement compositions. Additionally, the hydraulic cement compositions according to the invention exhibit good storage stability, for example, greater than one day, and, in certain embodiments, greater than one week, or, even more specifically, greater than one month, without setting, and do not require premixing by the user, for example, in a surgery setting. Further, the hardened cements obtained from the present compositions, methods, and articles of manufacture provide good in vivo performance in various applications. These and additional objects and advantages of the present invention will be more fully appreciated in view of the following detailed description.

BRIEF DESCRIPTION OF THE DRAWINGS

The following detailed description will be more fully understood when viewed together with the drawings, in which:

FIG. 1A: >100 µm; FIG. 1B: 100-200 µm; FIG. 1C: 200-400 µm; FIG. 1D: 400-600 µm; FIG. 1E: All sizes (no separation). In the materials of FIG. 1C and FIG. 1D, where larger grain sizes have been used, larger pores are clearly visibly throughout the set cement, whereas the materials of FIG. 1A and FIG. 1B have smaller pores.

DETAILED DESCRIPTION

Figure 1A:
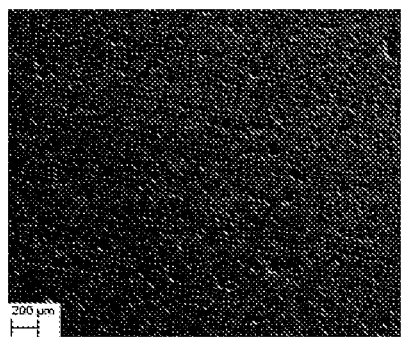
FIGS. 1A-1E show scanning electron micrograph (SEM) images (75×) of polished cross sections of hardened cement samples as described in Example 4, prepared using a powder to liquid (P/L) ratio of 4.2. The monocalcium phosphate (MCP) grain size is as follows.
Figure 1B:
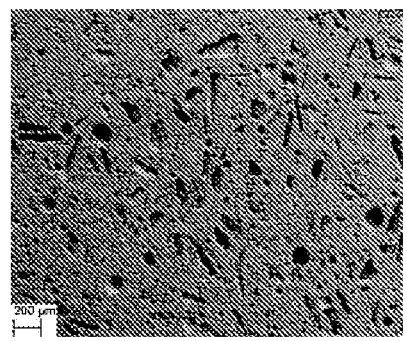
Figure 1C:
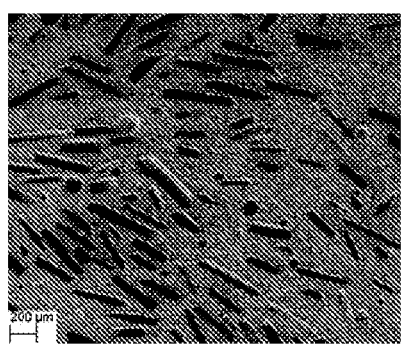
Figure 1D:
Figure 1E:
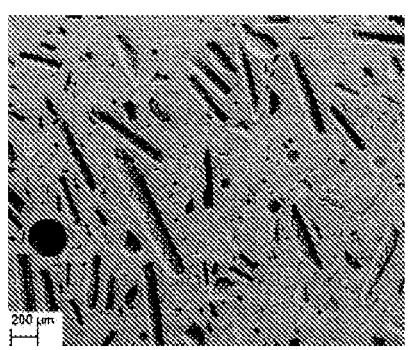

The hydraulic cement compositions of the present invention are suitable, in specific embodiments, for use in biomedical applications. The present description refers to use of the compositions for in vivo applications, for example in bone and tooth repair. It will be appreciated that the present compositions are suitable for other in vivo applications as well as for non-biomaterial applications.

In a first embodiment, the invention is directed to a refrigerated hydraulic cement composition which comprises a mixture of (a) β-tricalcium phosphate powder, (b) monocalcium phosphate comprising monocalcium phosphate anhydrous (MCPA), monocalcium phosphate monohydrate (MCPM), or a combination thereof, wherein a 0.1 g/ml saturated aqueous solution of the monocalcium phosphate has a pH less than 3.0, (c) non-aqueous water-miscible liquid, and (d) an aqueous hydrating liquid, wherein the aqueous hydrating liquid is included in an amount of about 1-50 volume percent, based on the combined volume of the non-aqueous water-miscible liquid and the aqueous hydration liquid. The refrigerated hydraulic cement composition is storage stable for greater than one day, without setting to a hardened cement.

Within the present disclosure, a refrigerated composition is a composition that is maintained at a temperature of not greater than about 5° C. In a specific embodiment, the composition is maintained at a temperature of less than about 0° C. In yet a further embodiment, the composition is frozen.

After hardening, the cement will form Brushite ($CaHPO_4 \cdot 2H_2O$) in temperature ranges of about 0-20° C. and Monetite ($CaHPO_4$) in temperature ranges of about 35-100° C. In the range between 20 and 35° C. a mixture of the two phases will form.

The MCPA and MCPM should exhibit a pH of below 3, and in further embodiments a pH of at least 2 in a saturated aqueous solution. In a more specific embodiment, the MCPA and MCPM should exhibit a pH of 2.5-2.8. The pH can typically be measured using a saturated aqueous solution of the powders (including glycerol), of about 0.1 g/mL. The pH of these solutions can then be measured using a standard pH meter. The indicated pH allows a faster setting and more complete chemical reaction during hydration of the cement. Below pH 2, MCPA and MCPM are less soluble in water; however, a lower pH will render cements with faster setting times and are therefore preferable.

In one embodiment, the monocalcium phosphate (MCP) consists essentially of MCPA, whereby significant amounts of MCPM, i.e., greater than about 25%, or greater than about 10%, or greater than about 5%, based on the weight of the monocalcium phosphate, are excluded. In another embodiment, the monocalcium phosphate consists of MCPA. The MCPA does not contain any crystal water as is the case with mono calcium phosphate monohydrate.

Generally, aqueous cement compositions mixed with water benefit from smaller particle sizes in the powder composition since this gives faster setting time and stronger cements. However, it has been discovered that premixed cements according to the invention are affected differently. When too small of particles sizes are used (i.e., mean grain size about 1 micrometer or less), the premixed cements are difficult to inject. For the premixed cements, the setting time is not affected to the same extent since in addition to the non-aqueous liquid dissolution rate, the water in the premix cement also controls the setting time. Therefore, smaller particles do not necessarily give faster setting times compared to cements with larger particles. Larger particles make the cement easier to inject than finer particle size powders. While not wishing to be bound by theory, it is believed that there is more non-aqueous liquid, for example, glycerol, (on average) between each powder grain, resulting in an easier shear of the cement paste and easier injection. In addition, the porosity is important to control since the porosity affects bone in-growth and the resorption time in vivo, Ginebra et al, "In vivo evaluation of an injectable Macroporous Calcium Phosphate Cement" *Journal of Materials Science-Materials in Medicine,* 18(2):353-361 (2007). By controlling the MCP particle size it is possible to control the porosity in the cement. In previous cement formulations, additional additives were added in order to obtain the desired porosity. In certain embodiments, additional aqueous hydration liquid, i.e., the surrounding body fluid (blood) in vivo use, may be exchanged with the non-aqueous liquid. During this liquid exchange, biological components will be transported into the cement, which are beneficial for faster bone in-growth and resorption of the cement. This liquid exchange will benefit from larger particle sizes that allow a quicker liquid exchange during hardening through the larger pores, which are formed when the MCPM and/or MCPA dissolves and since there is more glycerol (on average) between each powder grain.

Accordingly, in specific embodiments, at least 75%, at least 80%, at least 85%, or at least 90% of the MCP particles, or, more specifically, the MCPA particles, are of a size about 200-600 μm, or, more specifically about 400-600 μm. In such compositions, the specific particle sizes can, for example, be obtained by sieving. In specific embodiments, the powder to liquid ratio (P/L) is (weight/volume) about 3-5.5, more specifically about 3.5-5, to obtain a porous cement upon hardening, allowing for faster bone in-growth. In further embodiments, the MCP, or specifically, MCPA, particles size is about 1-400 μm, more specifically about 10-200 μm, and most specifically, about 10-100 μm, but larger than about 1 μm, and the P/L is about 2.5-5, more specifically about 3-4.5, for a cement with higher mechanical strength. In another specific embodiment, the particle size range is wide, ranging about 1-600 μm, and the P/L is from about 3-5.5, more specifically, about 3.5-5, for a cement with some larger pores allowing fast diffusion and that is mechanically strong.

In another embodiment, at least 75% of the monocalcium phosphate has a grain size of about 100 μm or less or about 600 μm or more.

In a specific embodiment, the β-TCP particle size can also be used to control properties. β-TCP has a lower solubility than MPC and the particle size of the β-TCP is therefore preferably smaller than the particle size of the MCP. Larger β-TCP particles make the cement easier to inject than finer particle size powders. Smaller particles will dissolve faster and thus allow a faster setting and the set cement will become stronger. The mean particle size of the β-TCP is preferably 1 to 40 μm, more preferably 3 to 30 um and most preferably 5 to 25 μm. The particle size distribution can for example be determined using laser diffraction.

In specific embodiments of the invention as described above, the relation between components (a) (β-TCP) and (b) (MCP) may vary as desired. In more specific embodiments, the weight ratio between components (a) and (b) is about 1:4-4:1, more specifically about 1:3-3:1, or more specifically about 2:3-3:1, to obtain a cement with higher mechanical strength.

Any suitable, non-aqueous water-miscible liquid may be employed to form the mixture. Exemplary liquids include, but are not limited to, glycerol, propylene glycol, poly (propylene glycol), poly(ethylene glycol) and combinations thereof, and related liquid compounds and derivatives, i.e., substances derived from non-aqueous water miscible substances, substitutes, i.e., substances where part of the chemical structure has been substituted with another chemical structure, and the like. Certain alcohols may also be suitable as mixing liquid. In a specific embodiment, the liquid is glycerol.

The aqueous hydrating liquid may comprise water, alone or together with any other polar liquid, such as protic solvents (e.g. alcohol). In specific embodiments, the aqueous hydrating liquid consists essentially of water or consists of water. The aqueous hydrating liquid can optionally have a pH within the range of 1-9. The aqueous hydrating liquid is included in an amount of about 1-50 volume %, more specifically, about 10-40 volume %, about 10-30 volume %, or about 15-30 volume %, based on the combined volume of the non-aqueous liquid and the aqueous hydrating liquid. The inclusion of the aqueous hydrating liquid in the hydraulic cement compositions of this embodiment of the present invention improves the mechanical properties of the set cement material. Furthermore, the hydration liquid makes the cement less viscous, thus improving the injectability. Additionally, the hydration liquid reduces the setting time of the hydraulic cement composition. Refrigeration of the cement prevents the composition from setting prematurely, as discussed below.

The powder to liquid weight to volume ratio (P/L) may suitably be in a range of from about 0.5 to about 10, more specifically from about 1 to about 7, and more specifically from about 2.5 to about 7, or from about 2.5 to about 5, or from about 3 to about 4.5, for better handling and mechanical strength.

By refrigerating the compositions containing both the non-aqueous water-miscible liquid and the aqueous hydrating liquid, storage stability of greater than one day, greater than one week, greater than one month, greater than three months, greater than six months, or greater than nine months, can be obtained. Additionally, the refrigerated compositions are easily injectable, for example, in vivo. A hardened cement is prepared by removing the refrigerated hydraulic cement composition from a refrigerated location and allowing the removed composition to reach room temperature (i.e., about 22° C.) or a temperature higher than room temperature. Once the composition reaches room temperature, the composition will remain injectable or formable for about 1-3 hours. Once the composition reaches a higher temperature, for example, body temperature, the composition will form a hardened cement in about 10-20 minutes, more specifically, about 10-15 minutes.

In a further embodiment, the hydraulic cement composition comprises porous β-tricalcium phosphate (β-TCP) granules. The porous β-TCP granules modify the resorption rate and bone remodelling of the hardened cement which is formed upon delivery and setting. The granules generally comprise agglomerated powders and the porosity of the granules comprises pores formed between individual powder grains in the agglomerates. In a specific embodiment, the granule size is from about 10 to about 3000 micrometers. In a further embodiment, the granule size is from about 10 to about 1000 micrometers and may be selected to optimize mechanical and/or biological properties of the resulting hardened cement. In a specific embodiment, the granule porosity is at most 80 volume % and the pore size is at most 500 micrometers, or, more specifically, at most 200 micrometers.

In specific embodiments, the weight ratio of porous β-TCP granules to calcium phosphate powder in the composition is in a range of about, 1:9 to about 6:1 or, more specifically, in a range of about 1:6 to about 1:1. In other specific embodiments, the weight ratio of porous β-TCP granules to powder in the composition is in a range about 1:3 to about 3:1, or, more specifically, in a range of about 2:1 to about 1:2.

The hydraulic cement compositions of the invention may also include agents that facilitate a fast diffusion of the non-aqueous liquid. In one embodiment, the agent comprises a surfactant, more specifically, a non-ionic surfactant, an example of which includes, but is not limited to, a polysorbate. The amount of surfactant may vary from about 0.01 to about 5 weight % of the powder composition, or, more specifically, from about 0.1 to about 1 weight %. See, for example, Shimada et al, "Properties of Injectable Apatite-Forming Premixed Cements", *Journal of Research of the National Institute of Standards and Technology*, 115(4): 240 (July-August 2010).

The hydraulic cement compositions of the invention may also include one or more porogens to provide a macroporous cement product. A macroporous cement product facilitates fast resorption and tissue in-growth. The porogen may include sugars and other fast-resorbing agents, and non-limiting examples include calcium sulphate, mannitol, poly (a-hydroxy ester) foams, sucrose, $NaHCO_3$, NaCl and sorbitol. The amount of porogen may suitably be from about 5 to about 30 weight % of the powder composition. The grain size of the porogens are typically in the range of 50 to 600 μm.

The hydraulic cement compositions of the invention may also include one or more non-toxic gelling agents to enhance cohesiveness and washout resistance of the compositions upon delivery. Exemplary gelling agents include, but are not limited to, chitosan, collagen, gum, gelatin, alginate, cellulose, polyacrylic acid (PAA), polyacrylic maleic acid (PAMA), polymethacrylic acid (PMA), neutral polyacrylic and/or polymethacrylic acid and/or polyacrylmaleic acid (e.g. Na-PAA, Na-PMA, Na-PAMA), hydroxypropylmethyl cellulose (HPMC), hydroxymethyl cellulose (HMC), polyvinylpyrrolidone (PVP), and carboxymethyl cellulose (CMC), and combinations thereof. The amount of gelling agent represents suitably from about 0.1 to about 7 weight % of the powder composition, more specifically from about 0.1 to about 2 weight %.

The hydraulic cement compositions may be delivered, for example, to an implant site when used as a biomaterial, using a syringe or spatula. The hydraulic cement compositions may be shaped in vivo, and optionally further hydrated in vivo. Optionally, a water-containing liquid can be added to the mixture before delivery, for example, before applying the material in vivo using a spatula although typically, addition of such aqueous liquid is not necessary and preferably is avoided as the refrigerated composition is in a "ready to use" form. Alternatively, the hydraulic cement compositions may be delivered to a mould to form a shaped body in vitro.

The hydraulic cement compositions can also be packaged in a vacuum package to reduce the amount of air voids in the mixture and thus increase the final strength of the hardened material. Air voids reduce the strength of the set material and reduction of air voids is therefore important. The hydraulic cement compositions may be conveniently mixed and packaged under vacuum conditions. Preferably, the hydraulic cement compositions are vacuum-mixed (e.g. in a Ross Vacuum Mixer Homogenizer).

Another embodiment of the invention comprises an article of manufacture comprising a hydraulic cement composition in a dispensing container, more specifically, a syringe. In another non-limiting example, the cement compositions is provided in a jar, then the cement is preferably applied using a special device, for example, a spatula or a spoon.

In a specific embodiment, the hydraulic cement composition comprises a Monetite-forming calcium phosphate powder composition. In a specific embodiment, the hydraulic cement composition comprises a calcium phosphate powder composition which forms a mixture of Monetite and Brushite. In these embodiments, the calcium phosphate powder composition is acidic, i.e., the pH of the hydraulic cement composition during setting is less than about 6.0.

The hydraulic cement composition may further comprise phosphoric acid, pyrophosphoric acid, or a mixture thereof, and/or one or more basic calcium phosphates, for example, anhydrous dicalcium phosphate, dicalcium phosphate dihydrate, octacalcium phosphate, α-tricalcium phosphate, β-tricalcium phosphate, amorphous calcium phosphate, calcium-deficient hydroxyapatite, non-stoichiometric hydroxyapatite, and tetracalcium phosphate.

The hydraulic cement composition may further comprise one or more calcium silicate powders, for example, $CaO-SiO_2$, $(CaO)_3SiO_2$, and/or $(CaO)_2SiO_2$, microcrystalline silica, and/or calcium aluminate powders, for example, $(CaO)_3Al_2O_3$, $(CaO)_{12}(Al_2O_3)_7$, $(CaO)Al_2O_3$, $CaO(Al_2O_3)_2$, and $CaO(Al_2O_3)_6$.

In another embodiment, the invention is directed to a method of manufacturing an implant, which method comprises (a) filling a mould with a mixture of (i) a nonhydrated cement powder composition, and (ii) a non-aqueous water-miscible liquid, (b) exposing the filled mould to a temperature greater than 25° C., for example, up to about and 120° C., and, optionally, an aqueous environment, to harden the mixture, (c) removing the mould to provide a shaped implant, and (d) exposing the shaped implant to an aqueous environment to remove non-aqueous water-miscible liquid from the shaped implant. In a specific embodiment, the cement powder composition comprises one of the cement powder compositions described above for use in the refrigerated compositions of the invention. In another specific embodiment, the cement powder composition comprises monocalcium phosphate comprising monocalcium phosphate anhydrous (MCPA), monocalcium phosphate monohydrate (MCPM), or a combination thereof, and forms monetite cement.

Bone tissue defects that cannot heal via tissue regeneration can be filled using autograph, allograph or synthetic scaffold materials. For large defects, e.g., defects in the cranium or in long bones, healing of the bone defect can be especially difficult. Scaffold strategies involve providing metals, polymers or ceramic materials, upon and/or into which new tissue can grow. Ceramic scaffolds are often preferred owing to their similarity with the host tissue, i.e., bone. Currently, typical manufacturing processes to obtain ceramic scaffolds with complex shapes are very complicated and time consuming. In general, two distinctly different ways to manufacture ceramic scaffolds are employed. According to a first "powder route" method, a ceramic powder is sintered, while, accordingly to a second "chemical bonding" route, ceramic is formed by chemical reaction (a cement setting and hardening reaction).

Currently, most ceramic scaffolds are produced using the powder route method. However, it is difficult to produce scaffolds with complex shapes due to the brittle nature of the materials. While different methods, e.g., three dimensional (3D) printing, have been developed to overcome problems with final shaping of the scaffolds, such methods give mechanically weak scaffolds and little control of surface roughness, both properties important for the final outcome of the scaffold. In addition, the methods are very time consuming. Attempts to use the chemical bonding route are limited, mainly due to the difficulties of obtaining a material which can be handled during processing and cleaned from manufacturing equipment and which allows enough working time before cement setting, i.e., once mixed with water, the cement quickly sets and is difficult to inject or otherwise deliver the material to the mould and to remove the material from manufacturing equipment. Accordingly, the methods of this embodiment of the invention can overcome these problems.

The nonhydrated cement powder composition is, in one embodiment, a calcium (Ca) salt precursor powder composition. The powder composition may be any of the powder compositions set forth in this disclosure, as described above, or any of the compositions described hereafter. In another embodiment, the mixture further comprises an aqueous hydration liquid. In specific embodiments, the mixture comprises about 1-50 volume percent, or more specifically, about 3-30 volume percent, of the aqueous hydration liquid, based on the combined volume of the non-aqueous water-miscible liquid, and the aqueous hydration liquid. The addition of an aqueous hydration liquid such as water to the mixture is particularly suitable for manufacturing implants of relatively larger sizes, while mixtures which do not contain an aqueous hydration liquid are particularly suitable for manufacturing smaller implants. Setting will initiate automatically, but for final hardening, a wet environment and/or elevated temperature is preferred. The method is advantageous in that a combined long working time and self-setting can be achieved and the viscosity of the cement is lower, facilitating the filling of the mould. However, with high amounts of added water, i.e. about 50% or more, the working time is significantly shorter and therefore cleaning of manufacturing equipment becomes more difficult as well.

The Ca-salt precursor composition may comprise one or more Ca-salts such as anhydrous dicalcium phosphate, dicalcium phosphate dihydrate, octacalcium phosphate, α-tricalcium phosphate, β-tricalcium phosphate, amorphous calcium phosphate, calcium-deficient hydroxyapatite, non-stoichiometric hydroxyapatite, tetracalcium phosphate and monocalcium phosphate monohydrate (MCPM), anhydrous monocalcium phosphate, phosphoric acid, pyrophosphoric acid, calcium sulphate (alfa or beta, preferably alfa) or calcium silicate (tricalciumsilicate, dicalciumsilicate or monocalcium silicate), calcium carbonate (aragonite, vaterite, calcite or amorphous) or combinations thereof. In a specific embodiment, the cement powder composition comprises monocalcium phosphate comprising monocalcium phosphate anhydrous (MCPA), monocalcium phosphate monohydrate (MCPM), or a combination thereof, and forms monetite cement. In a further embodiment, the cement powder composition comprises monocalcium phosphate and β-tricalcium phosphate, or, more specifically, the cement powder composition comprises a mixture of β-tricalcium phosphate powder and monocalcium phosphate comprising monocalcium phosphate anhydrous (MCPA), monocalcium phosphate monohydrate (MCPM), or a combination thereof, wherein a 0.1 g/ml saturated aqueous solution of the monocalcium phosphate has a pH less than 3.0. More specifically, a 0.1 g/ml saturated aqueous solution of the monocalcium phosphate has a pH less than 3.0 and greater than 2.0, or, specifically, has a pH of about 2.5-2.8.

Any suitable, non-aqueous water-miscible liquid may be employed. Exemplary liquids include, but are not limited to, glycerol, propylene glycol, poly(propylene glycol), poly (ethylene glycol) and combinations thereof, and related liquid compounds and derivatives, i.e., substances derived from non-aqueous water miscible substances, substitutes, i.e., substances where part of the chemical structure has been substituted with another chemical structure, and the like. Certain alcohols may also be suitable. In one embodiment, the liquid is selected from glycerol, propylene glycol, poly (propylene glycol), poly(ethylene glycol) and combinations thereof. In a specific embodiment, the liquid is glycerol. The purpose of the non-aqueous water-miscible liquid is to give a longer working time during the mould filling step, because if the material starts to set then it is impossible to accurately achieve the complex shape.

The mixture may further include porous β-tricalcium phosphate (β-TCP) granules. Porous β-TCP granules modify the resorption rate and bone remodelling of the hardened cement which is formed upon setting. The granules generally comprise agglomerated powders and the porosity of the granules comprises pores formed between individual powder grains in the agglomerates. In a specific embodiment, the granule size is from about 10 to about 3000 micrometers. In a further embodiment, the granule size is from about 10 to about 1000 micrometers and in a more specific embodiment, the granule porosity is at most 80 vol % and the pore size is at most 500 micrometers. The granule size may be selected to optimize mechanical and/or biological properties of the resulting hardened cement. In a specific embodiment, the weight ratio of porous β-TCP granules to cement powder in the mixture is in a range of about 1:4 to about 4:1, of about 1:3 to about 3:1, or, more specifically, of about 2:1 to about 1:2.

The composition may also include one or more agents that facilitate a fast diffusion of water into the paste in situ, preferably a non-ionic surfactant, as described above. The amount of surfactant is preferably from about 0.01 to 5 wt % of the powder composition, most preferably about 0.1-1 wt %.

In some formulations, salts may be dissolved into the liquid to obtain a fast or slower setting, e.g. citric acid, $H_3C_6H_5O_7$, disodium pyrophosphate, $Na_2H_2P_2O_7$, sulfuric acid, $H_2SO_4$, phosphoric acid, $H_3PO_4$, or the like. In one such embodiment, the hardening is then performed in a dry environment.

The compositions may also include one or more porogens as described above to give a macroporous end product to facilitate fast resorption and tissue in-growth. The pores give a good foundation for bone cells to grow in. Optionally, pores going through the implant system can be introduced by editing a computer model from a CT-scan thus ensuring sufficient blood flow, especially when the surface area of the implant is large.

The compositions may also include a non-toxic gelling agent as described above to enhance cohesiveness and washout resistance. The amount of gelling agent preferably is from about 0.1 wt % to 10 wt % of the powder composition, more preferably from about 0.1 wt % to 2 wt %.

The precursor powder (weight) to liquid (volume) ratio is about 0.5 to 10 as this gives optimal results, more specifically, about 2 to 6, even more specifically, about 3.5 to 4.5. The mean grain size of the precursor powder can be used to control the mechanical strength of the hardened material, normally grain sizes of below about 500 microns are used. Smaller grain sizes give higher mechanical strength than larger grain sizes. However, for the embodiments of the invention containing porous granules, the granule size may be larger but preferably is still below about 500 micrometer. Normally, granules do not participate in the setting reaction of the paste. They are added as ballast to the material and the presence of pores gives a better biological response to the material. Preferably, at least some of the pores in a granule should be large enough for cells to enter into the granule, normally above at least about 10 microns. Inevitably, there will also be smaller pores in the granules but they are of less importance for the cell integration.

In another embodiment of manufacturing an implant in accordance with the present embodiment of the invention, in the moulding step, a hydraulic cement composition comprises a mixture of non-aqueous liquid and water and a Brushite- or Monetite-forming calcium phosphate powder composition, which is subsequently injected into the mould and allowed to harden. One example of a Monetite-forming composition includes a 1:1 molar ratio of β-tricalcium phosphate (preferably a grain size ranging from about 0.1 to 100 micrometer) and monocalcium phosphate monohydrate (MCPM), or a 1:1 molar ratio of β-tricalcium phosphate (preferably a grain size ranging from about 0.1 to 100 micrometer) and anhydrous monocalcium phosphate (MCPA). The grain size of MCMP or MCPA may have a larger spread than the β-tricalcium phosphate, preferably ranging from about 1 to 800 micrometer, or, more specifically, from about 1 to 600 micrometer. A suitable powder to liquid ratio can be found in the range of about 3 to 5, preferably around 4.

In another embodiment of manufacturing an implant in accordance with the present invention, in the moulding step, a non-aqueous, hydraulic cement composition comprises a mixture of non-aqueous liquid, water, porous β-tricalcium phosphate (β-TCP) granules and a non-hydrated powder composition comprising at least one calcium phosphate powder.

Hardening is preferably performed at elevated temperatures, i.e., greater than about 25° C., more specifically, greater than about 40° C., or greater than about 50° C., up to about 120° C., and optionally under wet or moist conditions, i.e., in an aqueous environment. An example of a wet environment is a water bath. An example of a moist environment is a chamber where the relative humidity is greater than about 50%, more specifically, about 100%.

In an alternate embodiment, the precursor powder composition is basic (apatitic) and the mixture comprises (a) a basic calcium phosphate component comprising porous β-TCP granules and tetra calcium phosphate (TTCP) and/or amorphous calcium phosphate, and (b) an acidic phosphate, non-limiting examples of which include monocalcium phosphate monohydrate (MCPM), anhydrous monocalcium phosphate, phosphoric acid, pyrophosphoric acid or combinations thereof. The components of the apatitic precursor powder compositions are chosen such that (i) the pH of the cement paste during setting is higher then 6; and (ii) the end-product of the setting reaction comprises amorphous calcium phosphate hydrate, hydroxyapatite, ion-substituted hydroxyapatite, or combinations thereof.

In specific embodiments, the cement powder composition comprises a Brushite or Monetite-forming calcium phosphate powder composition, and, more specifically, the Brushite or Monetite-forming calcium phosphate powder composition comprises monocalcium phosphate monohydrate, anhydrous monocalcium phosphate, or a mixture thereof. In additional specific embodiments, the mixture comprises at least one calcium phosphate powder and further comprises porous β-tricalcium phosphate (β-TCP) granules, and more specifically, the at least one additional calcium phosphate powder comprises monocalcium phosphate monohydrate, anhydrous monocalcium phosphate, or a mixture thereof, and, in additional specific embodiments, the at least one additional calcium phosphate powder further comprises a basic powder comprising tetracalcium phosphate, octacalcium phosphate (OCP), α-tricalcium phosphate (α-TCP), β-tricalcium phosphate (β-TCP), amorphous calcium phosphate, calcium-deficient hydroxyapatite (HA), non-stoichiometric HA, ion-substituted HA, tetracalcium phosphate (TTCP) or combinations thereof. In additional specific embodiments, the cement powder composition comprises calcium silicate powder or calcium aluminate powder.

The following process describes one, non-limiting embodiment of the present methods:

1. Manufacture of a model of a bone defect. Using 3D-printing, a model of the defect is manufactured based on data from CT-scans.

2. Manufacture a mould for the scaffold (implant). The mould is preferably produced of a polymer that is easy to de-mould after setting, for example sodium alginate or polyether. One preferred mould material is silicone rubber, due to its high biocompatibility and easy handling. The model is used to manufacture the mould by applying the mould material onto the mould and letting the mould material set. Examples of suitable mould materials include Silagum, Silagum light (DMG Dental), and Silupran 2450 (Wacker Silicones). The first two are dental impression materials and the later is used for temporary implants.

3. Filling the mould with a mixture of a nonhydrated cement powder composition which is soluble or partly soluble in water, a non-aqueous water-miscible liquid, and optionally, an aqueous hydration liquid.

4. Letting the filled mould harden at temperatures above about 25° C. and up to about 120° C., optionally, in a moist or wet environment. Preferably, the material is set and hardened under an external pressure, e.g. using a mechanical press or the like. This produces a final product with higher mechanical strength.

5. Demoulding the sample and optionally letting the sample further harden in a moist or wet environment, preferably at elevated temperatures as described above.

6. Soaking of the samples to remove excess of the non-aqueous water-miscible liquid.

7. Optional final polishing of the samples.

8. Packing and sterilization using conventional sterilizing methods and packaging solutions.

The implant system can be attached to the host tissue via sutures and/or plates and screws and/or clamps or any other fixing means.

To increase the strength of the implant system, the ceramic material may be moulded onto a mesh of a more ductile material such as a polymer or a metal, e.g. titanium mesh.

The implant system can be used in tissue replacements (bone and soft tissue replacement) and in veterinary medicine.

According to another embodiment, the invention is directed to calcium silicate and/or calcium aluminate hydraulic cement compositions. More particularly, in a specific embodiment, a hydraulic cement composition comprises a mixture of (a) a non-hydrated powder composition comprising calcium silicate powder, (b) non-aqueous water-miscible liquid, and (c) a hydration liquid. When hydrated, the composition forms mainly a calcium silicate hydrate. In a specific embodiment, the powder composition comprises about 20-100 weight % calcium silicate, for example, CaO-$SiO_2$, $(CaO)_3SiO_2$, and/or $(CaO)_2SiO_2$, with a balance of one or more of the calcium based powders discussed in the earlier embodiments of the invention. In one embodiment, to optimize a clinically acceptable setting time, the composition includes $(CaO)_3SiO_2$ or $(CaO)_2SiO_2$ or combinations thereof, or, more specifically, $(CaO)_3SiO_2$. It is often difficult to obtain a 100% pure phase composition and therefore trace amounts of all calcium silicate phases may be present in the composition. The grain size of the calcium silicate powder is generally below about 200 micrometer, preferably below about 50 micrometer, to obtain an optimal combination of injectability (coarse powder) and strength (fine grain size).

In another specific embodiment, a hydraulic cement composition comprises a mixture of (a) a non-hydrated powder composition comprising calcium aluminate powder, (b) non-aqueous water-miscible liquid (c) a hydration liquid. The powder composition comprises one or more powders selected from the group consisting of $(CaO)_3Al_2O_3$, $(CaO)_{12}(Al_2O_3)_7$, $(CaO)Al_2O_3$, $CaO(Al_2O_3)_2$, and $CaO(Al_2O_3)_6$, with a balance of one or more of the calcium based powders discussed in the earlier embodiments of the invention. In a specific embodiment, wherein the setting time may be optimized, the calcium aluminate powder comprises one or more powders selected from the group consisting of $(CaO)_3Al_2O_3$, $(CaO)_{12}(Al_2O_3)_7$, and $(CaO)Al_2O_3$. In a more specific embodiment, the calcium aluminate powder comprises $(CaO)_{12}(Al_2O_3)_7$ and/or $(CaO)Al_2O_3$ and in a more specific embodiment, the calcium aluminate powder comprises $(CaO)Al_2O_3$. In one embodiment, the calcium aluminate is amorphous, more specifically amorphous $(CaO)_{12}(Al_2O_3)_7$. Upon hydration, a hardened cement comprising calcium aluminate hydrate is formed. The grain size of the calcium silicate powder is generally below 200 micrometer, preferably below 50 micrometer. This to obtain an optimal combination of injectability (coarse powder) and strength (fine grain size).

In a specific embodiment, the powder composition comprises at least about 10 weight %, or from about 10 to about 100 weight %, of calcium aluminate powder. In a more specific embodiment, the powder composition comprises at least about 50 weight percent of the calcium aluminate powder to provide high strength. In a further embodiment, the powder composition comprises from about 3 to about 60 weight %, specifically from about 3 to about 50 weight %, more specifically from about 10 to about 30 weight %, of an agent operable to increase radio-opacity of the composition. Examples of such agents include, but are not limited to, zirconium dioxide, barium sulfate, iodine and strontium compounds and combinations thereof. The increased radio-opacity provided by such an agent is important to increase safety during injection (high visibility compared to bone tissue) and follow up when set in vivo. The powder composition may also optionally include microcrystalline silica which may be added to control expansion properties of the material. In one embodiment, the powder composition comprises from about 0.1 to about 15 weight %, more specifically from about 0.1 to about 5 weight %, of microcrystalline silica.

The powder to liquid (i.e., non-aqueous water-miscible liquid and hydration liquid) weight to volume ratio (P/L ratio) in the calcium silicate and/or calcium aluminate-containing hydraulic cement compositions may suitably be in a range of from about 0.5 to about 10, more specifically from about 1 to about 7, and more specifically from about 2.5 to about 7, or from about 2.5 to about 6, for better handling and mechanical strength. These ratios are suitable even if two or more non-aqueous water-miscible liquids and/or hydration liquids are used in combination. Any suitable, non-aqueous water-miscible liquid may be employed. Exemplary liquids include, but are not limited to, glycerol, propylene glycol, poly(propylene glycol), poly (ethylene glycol) and combinations thereof, and related liquid compounds and derivatives, i.e., substances derived from non-aqueous water miscible substances, substitutes, i.e., substances where part of the chemical structure has been substituted with another chemical structure, and the like. Certain alcohols may also be suitable. In a specific embodiment, the liquid is glycerol. Any suitable hydrating liquid is employed. The hydration liquid may be any polar liquid, such as water or polar protic solvents (e.g. alcohol). The hydrating liquid is suitably water or an aqueous solution. The hydration liquid can optionally have a pH within the range of 1-9. The concentration of the hydration liquid, based on the combination of the hydration liquid and the non aqueous water miscible liquid combined, may suitably be in a range of 1 to 50% (v/v), more specifically from 2-40%, and more specifically from 3-30% for better mechanical strength and adequate handling properties.

The calcium silicate and/or calcium aluminate-containing hydraulic cement compositions may also include one or more porogens to give a macroporous end product to facilitate fast resorption and tissue in-growth. The pores give a good foundation for bone cells to grow in. The porogen may include sugars and other fast-resorbing agents, and non-limiting examples include calcium sulphate, mannitol, poly (a-hydroxy ester) foams, sucrose, $NaHCO_3$, NaCl and sorbitol. The amount of porogen may suitably be from about 5 to about 30 weight % of the powder composition. The grain size of the porogens are typically in the range of 50 to 600 μm.

The hydraulic cement compositions containing calcium silicate and/or calcium aluminate in the form of a premixed paste may be delivered, for example to an implant site when used as a biomaterial, using a syringe or spatula. The hydraulic cement compositions may be shaped in vivo, and subsequently be hydrated or be allowed to hydrate in vivo. Optionally, a water-containing liquid can be added to the premixed paste just before delivery in the operating room, for example, into a jar. The hydraulic cement compositions in the form of a premixed paste can also be packaged in a vacuum package to reduce the amount of air voids in the paste and thus increase the final strength of the hardened material. Air voids reduce the strength of the set material and reduction of air voids is therefore important. The hydraulic cement compositions may be conveniently mixed and packaged under vacuum conditions. Preferably the hydraulic cement compositions are vacuum-mixed (e.g. in a Ross Vacuum Mixer Homogenizer).

In one embodiment, a premix containing calcium silicate and/or calcium aluminate is formed of the cement composition components other than the aqueous hydration liquid. The hardened cement is then formed by contacting the premix with the aqueous hydration liquid and allowing the resulting mixture to set. The aqueous hydration liquid may be added to the premix, for example, by mixing prior to delivery of the cement composition to an environment of use. Alternatively, the aqueous hydration liquid may comprise a body fluid, i.e., saliva, blood or the like, which is contacted with the premix once the premix is delivered in vivo. Alternatively, the aqueous hydration liquid may be provided in the form of an aqueous bath, which is suitable, for example, for molding complex shapes with subsequent hardening in water-containing bath. The hardening can optionally be performed at elevated temperatures, i.e., greater than about 25° C., up to, for example, about 120° C., for faster hardening and can also be used to control the phase of the hardened material. Such hardened materials can for example be used as custom made implants or for implants with a complex geometry difficult to achieve via normal powder processing routes.

In another embodiment of the invention, the hydraulic cement compositions containing calcium silicate and/or calcium aluminate, or the premix thereof which omits the aqueous hydration liquid, may be provided as an article of manufacture and/or a component of a kit, for example in combination with a separately contained quantity of hydration liquid. In a specific embodiment, the kit comprises several prefilled syringes of the same or of various sizes. One non-limiting example is a kit with several 2 ml prefilled syringes. Another non-limiting example is a kit with several 1 ml prefilled syringes. Thus, another embodiment of the invention comprises an article of manufacture comprising a hydraulic cement composition in a dispensing container, more specifically a syringe.

In one embodiment, an article of manufacture comprises a first container containing a hydraulic cement premix composition comprising (a) a cement powder composition containing calcium silicate and/or calcium aluminate, and (b) a non-aqueous water-miscible liquid, and a second container containing a quantity of aqueous hydration liquid. In a specific embodiment, the first container and the second container may be in the form of a double barrel syringe. Suitably, such a syringe may additionally provide for mixing of the premix and aqueous hydration liquid prior to of upon dispensing. In another embodiment, the first container is a vacuum package. Suitably, the quantity of aqueous hydration liquid comprises about 1-50 volume percent of the combined volume of the non-aqueous water-miscible liquid and the aqueous hydration liquid.

The described hydraulic cement compositions containing calcium silicate and/or calcium aluminate are suitably employed as injectable in situ-setting biomaterials. The compositions can be used as any implant, more specifically as a bone implant, more specifically as dental or orthopedic implant. In a specific embodiment, the hydraulic cement compositions are suitable used as material in cranio maxillofacial defects (CMF), bone void filler, trauma, spinal, endodontic, intervertebral disc replacement and percutaneous vertebroplasty (vertebral compression fracture) applications.

Various embodiments of the invention are illustrated in the following Examples.

Example 1

This example shows the effect of the pH of monocalcium phosphate has on the setting properties of the cement formulation.

Monocalcium phosphate monohydrate and anhydrous from 5 different suppliers were evaluated. When the anhydrous form could not be obtained from the supplier, the MCPM was heated to 120° in order to form MCPA. The particle size of the tested MCPA and MCPM powders was in the range of 10-400 µm. Saturated aqueous solutions of the powders (including glycerol) were prepared (0.1 g/mL). The pH of these solutions was measured using a standard pH meter. The different MCPA and MCPM powders were then used in cement formulations prepared with a powder to liquid ratio of 3.5 g/mL. The cements were evaluated regarding setting time.

Setting Time (ST)

To evaluate setting time of the cements, they were injected in five cylindrical moulds, diameter 6 mm, height 3 mm. At t=0, the filled moulds were immersed in 37° C. phosphate buffered saline solution (PBS, pH 7.4, Sigma), to simulate in vivo conditions. The cement was considered to have set when the sample could support the 453.5 g Gillmore needle with a tip diameter of 1.06 mm without breaking.

The results are set forth in Table 1:

TABLE 1 pH and setting time using various MCPA and MCPM

| Supplier | pH | Setting time |
|---|---|---|
| Scharlau: MCPM | 2.8 | ~40 min |
| Scharlau: MCPA | 2.8 | ~40 min |
| Innophos MCPM | 3.5 | No setting |
| Innophos MCPA | 3.5 | No setting |
| HiMed, MCPM | 3.5 | No setting |
| HiMed, MCPA | 3.5 | No setting |
| Chempur, MCPM | 2.7 | ~40 min |
| Chempur, MCPA | 2.8 | ~40 min |
| Strem, MCPM | 2.5 | ~40 min |
| Strem, MCPA | 2.6 | ~40 min |

The results show the importance of pH of the MCPM or MCPA for the setting of the cement.

Example 2

This example shows that use of MCPA instead of MCPM increases the room temperature setting time of the cement formulation. The setting time in room temperature of the cement using MCPA was significantly longer than when using MCPM.

Cement Preparation

Two cement formulations were evaluated. Cement 1 consisted of monocalcium phosphate hydrate (Alpha Aesar, containing both MCPM and MCPA) and β-tri calcium phosphate (β-TCP, Sigma) in a molar ratio of 1:1. Anhydrous glycerol was used as mixing liquid. Cement 2 consisted of monocalcium phosphate anhydrous (MCPA) and β-tri calcium phosphate (β-TCP) in a molar ratio of 1:1. Anhydrous glycerol was used as mixing liquid. A powder to liquid ratio (P/L) of 4 (g/ml) was used for both cements. The MCPA was produced by heating the monocalcium phosphate hydrate powder to 110° C. for 24 h. A vacuum mixer was used to mix the cements.

Setting Time (ST)

To evaluate setting time, the cement was injected in four cylindrical moulds, diameter 6 mm, height 3 mm. At t=0, the filled moulds were immersed in 37° C. phosphate buffered saline solution (PBS, pH 7.4, Sigma), to simulate in vivo conditions. The cement was considered to have set when the sample could support the 453.5 g Gillmore needle with a tip diameter of 1.06 mm without breaking.

Compressive Strength (CS)

For CS measurements, the paste was injected into cylindrical moulds and immersed in 50 ml PBS at 37° C. in a sealed beaker. Sample dimensions were diameter 6 mm and height 12 mm. After 24 h, the samples were removed from the moulds and carefully polished to obtain the correct height and parallel surfaces. The maximum compressive stress until failure was measured.

Shelf Life 2 ml syringes were filled with cement, the syringes were then sealed and stored in a desiccator at 5 and 21° C. Cement was extruded from the syringes every 3 days until the cement had become too hard to be extruded.

The results are set forth in Table 2:

TABLE 2

Results

| Property | Cement 1 (MCPM + MCPA) | Cement 2 (MCPA) |
|---|---|---|
| Setting time | 30-40 min | 30-40 min |
| Compressive strength | 8-10 MPa | 8-10 MPa |
| Shelf life, 21° C. | 9 days | 27 days |

Example 3

This example shows a number of formulations using MCPA with different particle sizes and powder to liquid ratios. The results show that a larger grain size of the MCPA provides means to control the setting time, injection force and strength of the hardened material.

Cement Preparation

The cement consisted of monocalcium phosphate anhydrous (MCPA) and β-tri calcium phosphate (β-TCP), in a molar ratio of 1:1. Glycerol (anhydrous) was used as mixing liquid. The MCPA was sieved in order to obtain the following particle sizes: <100 µm, 100-200 µm, 200-400 µm, and 400-600 µm. MCPA was also used as received, containing all the mentioned particle sizes, hereby referred to as ALL. A vacuum mixer was used to mix the cements. All evaluated cement mixtures are listed in the Table 3:

TABLE 3

Evaluated Cements

| Particle size (µm) | P/L (g/ml) |
|---|---|
| <100 | 3.9, 4.2 |
| 100-200 | 4.0, 4.2 |
| 200-400 | 4.2 |
| 400-600 | 4.2, 4.4 |
| ALL | 4.2 |

Injectability

The injectability was evaluated by measuring the force needed to inject 2 ml of cement paste from a disposable syringe; barrel diameter 8.55 mm, outlet diameter 1.90 mm. The force applied to the syringe during the injection was measured and mean injection force from 10 to 30 mm displacement was calculated, this force is referred to as the injection force.

Setting Time (ST)

To evaluate setting time, the cement was injected in four cylindrical moulds diameter 6 mm, height 3 mm. At t=0, the filled moulds were immersed in 37° C. phosphate buffered saline solution (PBS, pH 7.4, Sigma), to simulate in vivo conditions. The cement was considered to have set when the sample could support the 453.5 g Gillmore needle with a tip diameter of 1.06 mm without breaking.

Compressive Strength (CS)

For CS measurements, the paste was injected into cylindrical moulds and immersed in 50 ml PBS at 37° C. in a sealed beaker. Sample dimensions were diameter 6 mm and height 12 mm. After 24 h, the samples were removed from the moulds and carefully polished to obtain the correct height and parallel surfaces. The maximum compressive stress until failure was measured.

The results are set forth in Table 4:

TABLE 4

Results

| Grain size (µm) | P/L (g/mL) | Injection force (N) | Setting time (min) | Compressive strength (MPa) |
|---|---|---|---|---|
| <100 | 3.9 | 120 ± 10 | 30-40 | 10-13 |
| <100 | 4.2 | 240 ± 10 | 25-35 | 12-13 |
| 100-200 | 4.0 | 100 ± 10 | 30-40 | 9-12 |
| 100-200 | 4.2 | 180 ± 10 | 25-35 | 10-12 |
| 200-400 | 4.2 | 100 ± 10 | 25-35 | 7-9 |
| 400-600 | 4.2 | 90 ± 10 | 30-40 | 6-8 |
| 400-600 | 4.4 | 180 ± 10 | 25-35 | 7-9 |
| ALL | 4.2 | 110 ± 10 | 25-35 | 8-10 |

Example 4

The example shows how properties such as injectablity, compressive strength and porosity can be controlled by varying the MCP particle size. By using a smaller a particle size, the injection force increases as well as the compressive strength whereas the porosity of the set cement decreases. Inversely, by using a larger particle size, the injection force decreases as well as the compressive strength and the pore size distribution of the cement shifts towards larger pores.

Cement Preparation

The cement consisted of monocalcium phosphate (MCP, Alfa Aesar) and β-tricalcium phosphate, mean particle size 12.9 µm measured by laser diffraction (β-TCP, Sigma), in a molar ratio of 1:1. The MCP was sieved in order to obtain the following particle sizes; <100 µm, 100-200 µm, 200-400 µm, and 400-600 µm. MCP was also used as received, containing all the mentioned particle sizes as well <5% of particles larger than 600 µm, hereby referred to as ALL. Glycerol (anhydrous) was used as mixing liquid. A vacuum mixer was used to mix the cements.

The evaluated cement mixtures are listed in Table 5:

TABLE 5

Cement Mixtures

| Particle size (µm) | P/L (g/ml) |
|---|---|
| <100 | 3.8, 4.2 |
| 100-200 | 4.0, 4.2 |
| 200-400 | 4.2 |
| 400-600 | 4.2, 4.4 |
| ALL | 4.2 |

Injectability

The injectability was evaluated by measuring the force needed to inject 2 ml of cement paste from a disposable syringe; barrel diameter 8.55 mm, outlet diameter 1.90 mm.

The force applied to the syringe during the injection was measured and mean injection force from 10 to 30 mm displacement was calculated, this force is referred to as the injection force.

Hardening Depth

The hardening depth of the cement after 50 minutes was evaluated on two cements, with particle sizes of 100-200 μm and 400-600 μm. The cements were injected into cylindrical split moulds, diameter 6 mm, height 12 mm open at one end, and immersed in 50 ml PBS at 37° C. After 50 min, the mould halves were separated and the thickness of the hardened surface layer was measured using a micrometer calliper.

Compressive Strength (CS)

For CS measurements, the paste was injected into cylindrical moulds and immersed in 50 ml PBS at 37° C. in a sealed beaker. Sample dimensions were diameter 6 mm and height 12 mm. After 24 h, the samples were removed from the moulds. Thereafter, the maximum compressive stress until failure was measured using a universal testing machine.

Scanning Electron Microscopy (SEM)

SEM analysis was made of the cross-sections of hardened cement to study the pore structure.

The results are set forth in Table 6:

TABLE 6

| Results | | | | |
|---|---|---|---|---|
| Grain size (μm) | P/L (g/mL) | Injection force (N) | Hardening depth (mm) | Compressive strength (MPa) |
| <100 | 3.8 | 90 ± 10 | | 10-12 |
| <100 | 4.2 | 200 ± 10 | 1.55 | 12-14 |
| 100-200 | 4.0 | 75 ± 10 | | 9-11 |
| 100-200 | 4.2 | 150 ± 10 | | 10-12 |
| 200-400 | 4.2 | 75 ± 10 | | 8-10 |
| 400-600 | 4.2 | 60 ± 10 | 1.77 | 6-8 |
| 400-600 | 4.5 | 160 ± 10 | | 7-9 |
| ALL | 4.2 | 80 ± 10 | | 11-13 |

Example 5

This example shows how the addition of mannitol to the cement composition affects the porosity, setting time and mechanical properties of the set cement. With no added mannitol, the porosity of the set cement is 50%, and with the addition of 30% mannitol, the porosity increases to ~70%. The results show that it is possible to control the porosity of the set cement via addition of pore forming agents. The cement is intended to be used either as in vivo injectable material or to harden in molds outside the body and then implanted in hardened form.

Cement Preparation

The cement consisted of an equimolar mixture of mono calcium phosphate (MCP, Alfa Aesar) and β-tri calcium phosphate (Sigma). Glycerol was used as mixing liquid. Mannitol was used as the porogen, particle size<400 μm. The mannitol powder was combined with the premixed powder at mannitol/(mannitol+premixed powder) mass fractions of 0%, 10%, 20%, 30%. The powder was then mixed thoroughly with glycerol at a powder to liquid ratio of 4 g/ml. After 24 h, the samples were removed from the mould and placed in the PBS solution for 2 days to dissolve the mannitol and form macropores.

Compressive Strength

For CS measurements, the paste was injected into cylindrical moulds and immersed in 50 ml PBS at 37° C. in a sealed beaker. Sample dimensions were diameter 6 mm and height 12 mm. After 24 h, the samples were removed from the moulds and placed in the PBS solution for 2 days to dissolve the mannitol and form macropores. Thereafter the maximum compressive stress until failure was measured using a universal testing machine.

Diametral Tensile Strength

For the diametral tensile strength (DTS) measurement, the samples measured 6 mm in diameter and 3 mm in height. The tensile strength was determined by loading the samples at 1 mm/min across a diameter producing tensile stresses perpendicular to the vertical plane passing through the center of the specimen. After each compressive test, the fracture load was recorded.

Density and Relative Porosity Measurements

The specimens (6 mm×12 mm) with various mannitol mass fractions were dried. Both apparent and true densities were calculated for each specimen, where apparent density included both the open and closed porosity in the volume of the sample, and true density included only the closed porosity in the volume of the structure. The bulk density or the apparent density of the specimens was calculated from the ratio of the specimen weight to the specimen volume. The volume was calculated by the specimen dimensions. The skeletal densities of the specimens were determined by the use of helium.

The results are set forth in Table 7:

TABLE 7

| Setting time, compression strength and diametral tensile strength | | |
|---|---|---|
| Mannitol Mass fraction (%) | Compression strength (MPa) | Diametral tensile strength (MPa) |
| 0 | 9.6 (1.2) | 1.91 (0.18) |
| 10 | 5.2 (0.7) | 0.73 (0.18) |
| 20 | 1.6 (0.17) | 0.36 (0.12) |
| 30 | 0.30 (0.07) | — |

Porosity

Figure 2:
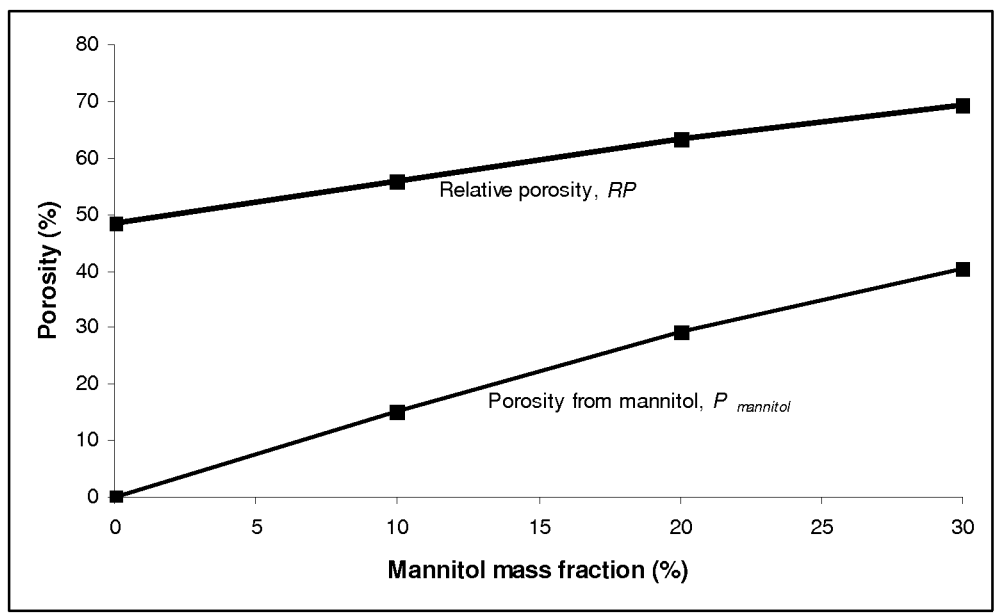
FIG. 2 shows the relative porosity and porosity from mannitol of premixed cement as a function of mannitol mass fraction, as described in Example 5.

Table 8 shows the bulk and true densities of the samples. Bulk density is found to range from 1.45 to 0.87 g/cm$^3$. FIG. 2 shows the relative porosity and porosity from mannitol as a function of mannitol mass fraction.

TABLE 8

| Density measurements of the premixed cement | | |
|---|---|---|
| Mannitol mass fraction (%) | Bulk density (g/cm$^3$) | Pycnometer density (g/cm$^3$) |
| 0 | 1.45 (0.02) | 2.83 (0.001) |
| 10 | 1.23 (0.33) | 2.82 (0.003) |
| 20 | 1.03 (0.17) | 2.80 (0.002) |
| 30 | 0.87 (0.01) | 2.83 (0.006) |

Example 6

This example demonstrates the effect of adding a hydration liquid such as water to a premixed cement formulation. The addition of 5-15% water increases the compressive strength significantly and also decreases the injection force and the setting time.

Cement Preparation

A first type of cement consisted of monocalcium phosphate anhydrous (MCPA, grain size below 600 micrometer) and β-tricalcium phosphate (β-TCP, Sigma, grain size below 40 micrometer), in a molar ratio of 1:1. Glycerol (anhydrous) was used as a mixing liquid with a water concentration of 0, 7.5, 15, 22.5 and 30% (v/v). The powder to glycerol ratio was 4 (g/mL) A vacuum mixer was used to mix the cements. The MCPA was obtained by heating monocalcium phosphate hydrate (Alfa Aesar) to 110° C. for 24 hours.

A second type of cement consisted of calcium trisilicate $(CaO)_3SiO_2$ (C3S, grain size below 30 micrometer) and (β-TCP, Sigma, grain size below 40 micrometer) and $CaCl_2$, in a molar ratio of 5:1:0.1. Glycerol (anhydrous) was used as mixing liquid with a water concentration of 0 and 30% (v/v). The powder to liquid ratio was 4 (g/mL). A vacuum mixer was used to mix the cements. The injectability was not studied for the cement.

A third type of cement consisted of calcium monoaluminate $CaOAl_2O_3$ (CA, grain size below 30 micrometer), Zirconia, grain size below 40 micrometer, LiCl and microsilica in a molar ratio of 4:1:0.1:0.5. Glycerol (anhydrous) was used as mixing liquid with a water concentration of 0 and 30% (v/v). The powder to liquid ratio was 4 (g/mL). A vacuum mixer was used to mix the cements. The injectability was not studied for the cement.

Injectability

The injectability was evaluated by measuring the force needed to inject 2 ml of cement paste from a disposable syringe; barrel diameter 8.55 mm, outlet diameter 1.90 mm. The force applied to the syringe during the injection was measured and mean injection force from 10 to 30 mm displacement was calculated, this force is referred to as the injection force.

Setting Time (ST)

To evaluate setting time of the cement, the cement was injected in four cylindrical moulds diameter 6 mm, height 3 mm. At t=0, the filled moulds were immersed in 37° C. phosphate buffered saline solution (PBS, pH 7.4, Sigma), to simulate in vivo conditions. The cement was considered to have set when the sample could support the 453.5 g Gillmore needle with a tip diameter of 1.06 mm without breaking.

Compressive Strength (CS)

For CS measurements, the paste was injected into cylindrical moulds and immersed in 50 ml PBS at 37° C. in a sealed beaker. Sample dimensions were diameter 6 mm and height 12 mm. After 24 h, the samples were removed from the moulds and carefully polished to obtain the correct height and parallel surfaces. The maximum compressive stress until failure was measured.

The results are set forth in Tables 9-11:

TABLE 9

| Calcium phosphate cement | | | |
| --- | --- | --- | --- |
| Water (%) | Injection force (N) | Setting time (min) | Compressive strength (MPa) |
| 0 | 110 | 30-35 | 6-8 |
| 7.5 | 35 | 15-20 | 10-13 |
| 15 | 15 | 10-15 | 10-14 |
| 22.5 | 15 | 9-12 | 8-10 |
| 30 | 10 | 4-8 | 5-7 |

TABLE 10

| Calcium silicate cement | | |
| --- | --- | --- |
| Water (%) | Setting time (min) | Compressive strength (MPa) |
| 0 | >240 | n.d. (too long setting time) |
| 30 | <120 | 50 |

TABLE 11

| Calcium aluminate cement | | |
| --- | --- | --- |
| Water (%) | Setting time (min) | Compressive strength (MPa) |
| 0 | ~120 | 60 |
| 30 | <30 | 80 |

The results shows that the addition of a hydration liquid such as water it is possible to increase the strength at the same time as the setting time is reduced. The injectability of the cements were not studied closely however the viscosity of the cements containing water were less viscous then the non-aqueous mixtures and easier to inject into the sample moulds.

Example 7

A series of experiments were performed to study the influence of hardening temperature on the mechanical properties of the cements.

Cement Formulation

The cement consisted of monocalcium phosphate anhydrous (MCPA) and β-tri calcium phosphate (β-TCP, Degradeble Solutions), in a molar ratio of 1:1. Glycerol (anhydrous) was used as mixing liquid with a water concentration of 0, 7.5, 15, 22.5 and 30% (v/v). The powder to liquid ratio was 4 (g/mL) A vacuum mixer was used to mix the cements. The MCPA was obtained by heating monocalcium phosphate hydrate (MCPM, Alfa Aesar) to 110° C. for 24 hours.

Compressive Strength (CS)

For CS measurements, the paste was injected into cylindrical moulds and immersed in 50 ml PBS at 37° C. in a sealed beaker. Sample dimensions were diameter 6 mm and height 12 mm. After 24 h, the samples were removed from the moulds and carefully polished to obtain the correct height and parallel surfaces. The maximum compressive stress until failure was measured. The results are set forth in Table 12:

TABLE 12

| Results | | |
| --- | --- | --- |
| P/L | Water (%) | Compressive strength (MPa) |
| 4.1 | 18 | 27[1], 29[3] |
| 4.3 | 19 | 23[1], 26[2], |

[1]Hardened at 37° C.
[2]Hardened at 60° C.
[3]Hardened at 90° C.

The results showed that an increase in compressive strength is obtained for higher hardening temperatures. For the embodiments that include forming an implant and providing it in hardened state in vivo, an increase in hardening temperature gives a stronger product. Also, it was noted that the hardening is faster for higher hardening temperatures.

Example 8

This example demonstrates the preparation of an implant using a method of the invention.

Figure 3:
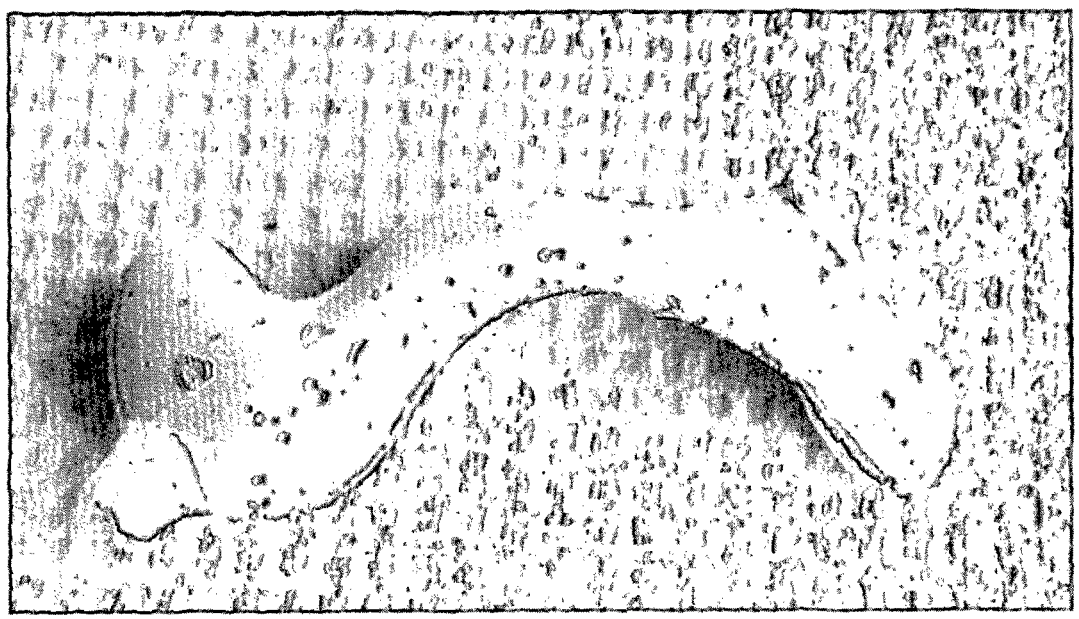
FIG. 3 shows a complex shaped implant produced according to a method of the invention as described in Example 8.
Figure 4:
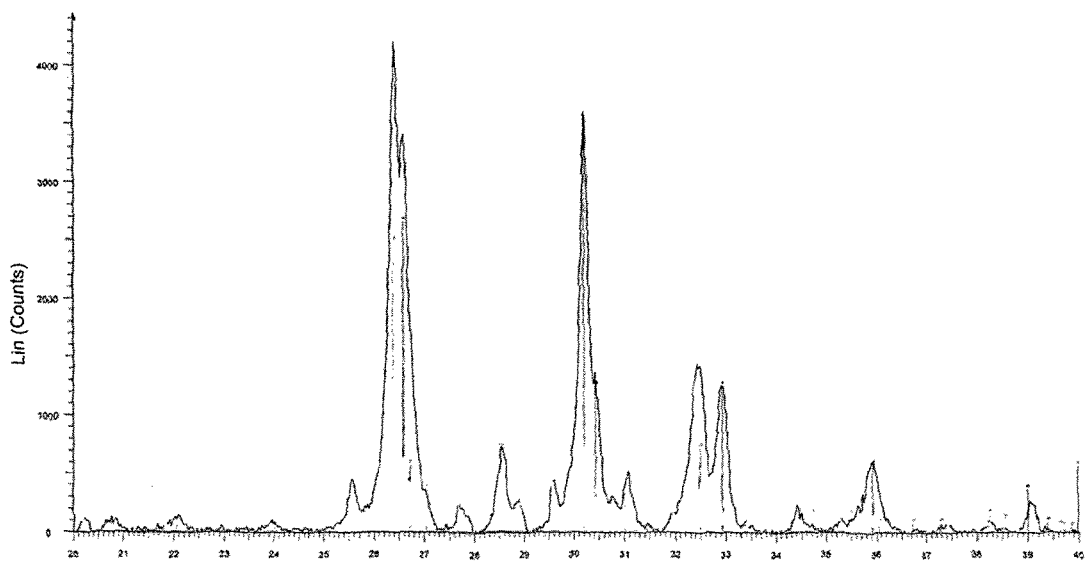
FIG. 4 shows an X-ray diffraction pattern of the implant material produced according to a method of the invention as described in Example 8.

From CT-X-ray images, a replica of a Lateral Orbital Zygoma was manufactured. A silicone rubber mould was then produced using the replica. Subsequently, a Monetite-forming paste was injected into the mould and allowed to harden in a water bath at 60° C. The paste had the following composition: monocalcium phosphate anhydrous (MCPA) with a grain size>400 μm and β-tricalcium phosphate (β-TCP) mixed in a molar ratio of 1:1. Glycerol with 10% (v/v) water was used as mixing liquid and the powder to liquid ratio was 4 g/mL. The cement was mixed using a Renfert Twister vacuum mixer in the following steps: Step 1: Glycerol+Water+MCPA, Step 2: Add ~60% of β-TCP, and Step 3: Add remaining β-TCP. After mixing, the paste was transferred into a syringe which was used to fill both halves of the mould. The viscosity of the cement will allow the cement to flow out so that it fills the mould well. If there is any excessive cement it can be removed using a spatula. The hardening was performed at 60° C. The implant was removed from the mould after 1 hour. In order to remove the glycerol from the composition, the implant was then soaked in a water bath. After the demoulding and soaking, some final polishing of irregularities was performed. The implant is shown in FIG. 3. After polishing, the implant was dried at 100° C. The elemental composition of the hardened implant was measured using X-Ray diffraction (XRD), the results of which are shown in FIG. 4 and indicate that the implant was composed of mainly Monetite after hardening.

Example 9

This example demonstrates the preparation of another implant using a method of the invention.
From CT-X-ray images, a replica of a part of a frontal bone was manufactured. A silicone rubber mould was then produced using the replica. Subsequently a Monetite forming paste was injected into the mould and allowed to harden in a dry environment at 90° C. The paste had the following composition: monocalcium phosphate anhydrous (MCPA) with a grain size>200 μm and β-TCP, mean grain size~11 micrometer, mixed in a molar ratio of 1:1. Glycerol with 15% (v/v) water was used as mixing liquid and the powder to liquid ratio was 3.4 g/mL. The cement was mixed using a Renfert Twister vacuum mixer in the following steps: Step 1: Glycerol+Water+MCPA, Step 2: Add ~60% of β-TCP and Step 3: Add remaining β-TCP. After mixing, the paste was transferred into a syringe which was used to fill both halves of the mould. Thereafter, a titanium mesh was placed in the cement in one of the moulds before the mould halves were joined. The viscosity of the cement allows the cement to flow out so that it fills the mould well. If there is any excessive cement it can be removed using a spatula. The hardening was performed at 90° C. The implant was removed from the mould after 1 hour. In order to remove the glycerol, the implant was then soaked in a water bath.

The specific examples and embodiments described herein are exemplary only in nature and are not intended to be limiting of the invention defined by the claims. Further embodiments and examples, and advantages thereof, will be apparent to one of ordinary skill in the art in view of this specification and are within the scope of the claimed invention.

What is claimed is:
1. A refrigerated hydraulic cement composition, comprising a mixture of
    (a) β-tricalcium phosphate powder,
    (b) monocalcium phosphate comprising monocalcium phosphate anhydrous (MCPA), monocalcium phosphate monohydrate (MCPM), or a combination thereof, wherein a 0.1 g/ml saturated aqueous solution of the monocalcium phosphate has a pH less than 3.0,
    (c) non-aqueous water-miscible liquid, and
    (d) an aqueous hydrating liquid,
        wherein the aqueous hydrating liquid is included in an amount of about 1-50 volume percent, based on the combined volume of the non-aqueous water-miscible liquid and the aqueous hydration liquid, and
        wherein the refrigerated hydraulic cement composition is refrigerated at a temperature not greater than about 5° C., is storage stable for greater than one month without setting, and forms Monetite ($CaHPO_4$) upon hardening at a temperature of about 35-100° C.

2. The refrigerated hydraulic cement composition of claim 1, wherein a 0.1 g/ml saturated aqueous solution of the monocalcium phosphate has a pH less than 3.0 and greater than 2.0.

3. The refrigerated hydraulic cement composition of claim 1, wherein a 0.1 g/ml saturated aqueous solution of the monocalcium phosphate has a pH of about 2.5-2.8.

4. The refrigerated hydraulic cement composition of claim 1, wherein the composition has a powder (weight) to liquid (volume) ratio of about 0.5-10, wherein the liquid comprises (c) the non-aqueous water-miscible liquid and (d) the aqueous hydrating liquid.

5. The refrigerated hydraulic cement composition of claim 1, wherein the composition has a powder (weight) to liquid (volume) ratio of about 2-5, wherein the liquid comprises (c) the non-aqueous water-miscible liquid and (d) the aqueous hydrating liquid.

6. The refrigerated hydraulic cement composition of claim 1, wherein at least about 90% of the monocalcium phosphate powder has a grain size in a range of about 1-600 μm, wherein the monocalcium phosphate powder has grain sizes in each of the ranges of <100 μm, 100-200 μm, 200-400 μm, and 400-600 μm, and wherein the powder (weight) to liquid (volume) ratio is about 3-5.5, wherein the liquid comprises (c) the non-aqueous water-miscible liquid and (d) the aqueous hydrating liquid.

7. The refrigerated hydraulic cement composition of claim 6, wherein at least 75% of the monocalcium phosphate has a grain size of about 100 μm or less or about 600 μm or more.

8. The refrigerated hydraulic cement composition of claim 1, wherein at least about 90% of the monocalcium phosphate powder has a grain size in a range of about 400-600 μm and the powder (weight) to liquid (volume) ratio is about 3.5-5, wherein the liquid comprises (c) the non-aqueous water-miscible liquid and (d) the aqueous hydrating liquid.

9. The refrigerated hydraulic cement composition of claim 1, wherein at least about 90% of the monocalcium phosphate powder has a grain size in a range of about 10-200 μm and the powder (weight) to liquid (volume) ratio is about 3-4.5, wherein the liquid comprises (c) the non-aqueous water-miscible liquid and (d) the aqueous hydrating liquid.

10. The refrigerated hydraulic cement composition of claim 1, wherein at least about 90% of the monocalcium phosphate powder has a grain size in a range of about 10-100 µm and the powder (weight) to liquid (volume) ratio is about 3-4.5, wherein the liquid comprises (c) the non-aqueous water-miscible liquid and (d) the aqueous hydrating liquid.

11. The refrigerated hydraulic cement composition of claim 1, wherein the weight ratio of (a) β-tricalcium phosphate powder to (b) monocalcium phosphate powder is from about 1:4 to about 4:1.

12. The refrigerated hydraulic cement composition of claim 1, wherein the β-tricalcium phosphate powder has a mean particle size of about 1-40 µm.

13. The refrigerated hydraulic cement composition of claim 1, further comprising porous β-tricalcium phosphate granules.

14. The refrigerated hydraulic cement composition of claim 1, wherein the non-aqueous water-miscible liquid comprises glycerol, propylene glycol, poly(propylene glycol), poly(ethylene glycol), or a combination of two or more thereof.

15. The refrigerated hydraulic cement composition of claim 1, wherein the non-aqueous water-miscible liquid comprises glycerol and the aqueous hydration liquid is water.

16. The refrigerated hydraulic cement composition of claim 1, wherein the aqueous hydrating liquid is included in an amount of about 3-30 volume percent, based on the combined volume of the non-aqueous water-miscible liquid and the aqueous hydration liquid.

17. The refrigerated hydraulic cement composition of claim 1, further comprising one or more of a surfactant, a porogen and a gelling agent.

18. The refrigerated hydraulic cement composition of claim 1, comprising about 5-30 weight percent of porogen comprising a powder having a grain size in the range of 50-600 µm.

19. The refrigerated hydraulic cement composition of claim 1, wherein the composition is refrigerated at a temperature below 0° C.

20. The refrigerated hydraulic cement composition of claim 1, wherein the refrigerated hydraulic cement composition is storage stable for greater than three months without setting.

21. The refrigerated hydraulic cement composition of claim 1, wherein the refrigerated hydraulic cement composition is storage stable for greater than six months without setting.

22. A method of preparing a hardened cement, comprising removing the refrigerated hydraulic cement composition of claim 1 from a refrigerated location and allowing the removed composition to reach room temperature or a temperature higher than room temperature.

23. An article of manufacture comprising a refrigerated container filled with the refrigerated hydraulic cement composition of claim 1.

24. The article of manufacture of claim 23, wherein the container is a syringe.

25. The article of manufacture of claim 23, wherein the container is a vacuum package.

26. A method of manufacturing an implant, comprising (a) removing the refrigerated hydraulic cement composition of claim 1 from a refrigerated location, (b) filling a mould with the composition, (c) exposing the filled mould to a temperature greater than 25° C. to harden the composition, (d) removing the mould to provide a shaped implant, and (e) exposing the shaped implant to an aqueous environment to remove non-aqueous water-miscible liquid from the shaped implant.

27. The method of claim 26, wherein the mould comprises silicone rubber.

28. The method of claim 26, wherein the mould is prepared by covering a model with a polymer which forms the mould, allowing the polymer to set, and removing the mould from the model.

29. The method of claim 26, wherein the model is formed by three dimensional printing of data from a computed tomography (CT) scan.

* * * * *

UNITED STATES PATENT AND TRADEMARK OFFICE
CERTIFICATE OF CORRECTION

| | | |
|---|---|---|
| PATENT NO. | : 9,676,665 B2 | Page 1 of 1 |
| APPLICATION NO. | : 14/343105 | |
| DATED | : June 13, 2017 | |
| INVENTOR(S) | : Håkan Engqvist et al. | |

It is certified that error appears in the above-identified patent and that said Letters Patent is hereby corrected as shown below:

On the Title Page

Item "(63) Related U.S. Application Data", Line 2, delete "which is a".

Item "(63) Related U.S. Application Data", Line 4, delete "which is a".

Signed and Sealed this
Fifth Day of September, 2017

Joseph Matal
*Performing the Functions and Duties of the*
*Under Secretary of Commerce for Intellectual Property and*
*Director of the United States Patent and Trademark Office*